United States Patent [19]
Caskey

[11] Patent Number: 5,646,710
[45] Date of Patent: Jul. 8, 1997

[54] OPHTHALMOLOGICAL SELF-TEST UNIT FOR EVALUATING MACULAR DEGENERATION

[76] Inventor: Patrick Caskey, 5111 Foothill Ranch Rd., Santa Rosa, Calif. 95404

[21] Appl. No.: 582,610

[22] Filed: Jan. 3, 1996

[51] Int. Cl.$^6$ ................ A61B 3/02; A61B 3/00
[52] U.S. Cl. .............. 351/223; 351/200; 351/243
[58] Field of Search ........................ 351/222, 223, 351/224, 237, 243, 200; 40/642; 248/309.4

[56] References Cited

U.S. PATENT DOCUMENTS

| | | | |
|---|---|---|---|
| 3,787,112 | 1/1974 | Lyons | 351/223 |
| 4,063,807 | 12/1977 | Gelius et al. | 351/224 |
| 4,310,978 | 1/1982 | Stern | 40/600 |
| 4,346,968 | 8/1982 | Melin et al. | 351/223 |
| 5,067,806 | 11/1991 | Kwasman | 351/243 X |

*Primary Examiner*—Huy Mai
*Attorney, Agent, or Firm*—Fish & Richardson P.C.

[57] ABSTRACT

An improved ophthalmological self test unit for assisting in the self evaluation of the degenerative effects of certain eye disorders. The self diagnostic ophthalmological device includes a grid area having a re-writable surface which is fixably attached to a magnetic backed material for ease of attachment to any metallic surface such as might often be found on a refrigerator. Disposed on the grid surface is a central focusing means for assisting in the focusing of a patient's attention to the central portion of the high contrast grid structure. In an alternative embodiment a polar grid is utilized along with the central focusing means mounted upon the magnetic backed material.

14 Claims, 7 Drawing Sheets

PRIOR ART

OPHTHALMOLOGICAL SELF-TEST UNIT FOR EVALUATING MACULAR DEGENERATION

FIELD OF THE INVENTION

The present invention relates generally to ophthalmological diagnostic equipment and particularly to an ophthalmological self-test unit which combines features of a standard Amsler grid with an attention focusing device in a convenient package for use in assisting a patient to consistently evaluate macular degeneration over time.

BACKGROUND OF THE INVENTION

Macular degeneration is a retinal disease which is the leading cause of central vision loss among people over the age of 65. Macular degeneration is a process of wear and tear in the macula, the portion of the retina responsible for sharp central vision and color perception. It usually affects both eyes, causing vision loss which may be either gradual or abrupt.

Referring to FIG. 1, a cross sectional view of a human eye is shown. The human eye is designed for panoramic viewing, allowing an individual to see objects straight ahead as well as to the side. As light enters the eye 10, it passes through the cornea 11 and pupil 12, and is focused by lens 13 into an image on retina 14. This image is converted by the retina into electrical impulses which are transmitted via optic nerve 15 to the brain. Macula 16 is the particular portion of the retina at which sharp central vision is processed.

The macula consists of multiple layers as is shown in FIG. 2. Innermost layer 18 of macula 16 is comprised of light sensing cells which produce sharp central vision. Two underlying layers nourish and help remove waste materials from these light sensing cells. The light sensing cells or "cones" as they are commonly referred to, are responsible for color perception and central vision. These cones shed their outer segments as waste products through normal metabolism. Second layer 20, known as the "retinal pigment epithelium", nourishes the cones and digests these shed outer segments during the day. Finally, third layer 22, known as the "choroid", comprises blood vessels that transport nutrients and carry away waste material from the macula region.

Macular degeneration is the common name for the age-related disease where macular retinal pigment epithelium cells function less well than normal. As a result, waste removal and nutrition of the cones suffers, causing central vision loss. Macular degeneration can be further classified into two varieties: a "dry type" and a "wet type". Dry type macular degeneration occurs when the outer segments of the light sensing cones, which are continuously being shed, are unable to be digested by the pigment epithelium layer of the macula. Consequently the pigment epithelium layer swells and eventually dies after accumulating too much undigested material from the cones. Yellowish deposits of this waste material gradually develop under the retina between the choroid and pigment epithelium. In this "dry type" macular degeneration, the vision loss is characterized by gradual blurring or partial obscuration of central vision as a result of parts of the macula having begun to die, creating areas where the cones are no longer functional. Clinically, the person suffering from this type of the disease may experience relatively mild central visual distortion with straight lines appearing bent or wavy.

In the second or "wet" type of this disorder, more severe and sudden vision loss may occur. This sort occurs when abnormal new blood vessels or "neovascular membranes" grow from the choroid through the damaged pigment epithelium and under the macula. These neovascular membranes are fragile and are prone to hemorrhage which results in severe distortion of the macular tissue. As a result, the light sensing cells (cones) become separated from their source of nutrients and suffer further damage due to eventual scarring as the hemorrhage contracts over time. With this type of disorder, dark or "missing" spots in the central vision may occur rapidly and with little warning due to these hemorrhagic changes. Fortunately, intervention with laser therapy early in this process may often prevent additional vision loss.

In order to detect changes early enough such that laser is beneficial, doctors use a variety of tests designed to evaluate the health of the macula. One such test is termed the "Amsler grid" and utilizes a uniform grid pattern of crossing lines to test central vision. The use of this grid reveals distortions and other abnormalities in the central field of vision. A patient once having been diagnosed with macular degeneration is typically required to monitor their vision with an Amsler grid on a daily basis in order to detect subtle signs of increasing distortion which may indicate an evolving neovascular membrane. Since this "wet" form of the disease may occur suddenly and with rapid vision loss, daily follow up is essential to ensure that intervention with laser treatment is instituted early enough to help prevent further visual damage.

The Amsler grid is known in the art (See FIG. 3). The use of the Amsler grid requires that a patient stand about a foot away from the grid itself, and, while wearing one's own glasses, covering or closing one eye while focusing on the center of the grid. In order for the Amsler grid to be effective, the patient must note any changes that occur over time and repeat the above process on a daily basis. While Amsler grids have been known for years in the art, the use of the grid in a practical setting by patients has revealed a number of every day problems.

Because of the nature of this degenerative eye disorder, daily use is required in order to track changes associated with the disorder such that early effective treatment can be implemented. As such, the grid must be accessible and easy to use in order to encourage use of the product. Accordingly, any improvements to the design of the grid which would improve the overall accessibility and ease of use would facilitate regular use. Use by patients has revealed that improvements to the basic grid design which facilitate the daily use of the device result in more consistent use of the product.

Secondly, the grid must also be sufficiently sized to accommodate the self testing of both the user's central and peripheral vision. A grid which is too small won't allow for the evaluation of a sufficient field of vision, yielding inaccurate or incomplete test results. However, the grid must not be so large as to become a nuisance to manipulate or store.

The degenerative nature of the eye disorder also requires that a patient be able to monitor the progress of the disease by somehow recording the particular areas of concern associated with each of the patient's eyes for a given baseline time frame, in order to determine whether or not any further damage has arisen. While the original grids were mass produced on paper products, any improvement which would assist the patient to identify and log the current eye condition as compared to a baseline condition would be desirable in order to help the patient in evaluating changes to his or her vision.

As described previously, the basic architecture of the Amsler grid includes a grid area which is utilized by the patient to assist in the evaluation of their vision. In practice patients have suggested that because of the poor contrast of the fixation target of the grid, that they often find themselves, and their eye that they are testing, wandering after but a few brief seconds when using the grid. Accordingly, any means of helping to assist a patient to keep their attention focused toward a single central location on the grid would assist in improving the accuracy of the self diagnostic tool.

The present invention improves on the prior art by providing a central attention focusing means which is designed to hold the patient's attention squarely centered on the grid so as to allow for a more accurate self diagnosis. The present invention includes an erasable re-writable surface to assist patients in identifying changes to their vision and progression of the disorder. The present invention also packages the grid, central focusing means and re-writable surface in a package which will assist the patient in performing the test on a daily basis, helping to remind the patient to conduct the self diagnosis while minimizing the possibility of loss of the grid itself and the baseline information upon which is stored.

SUMMARY OF THE INVENTION

It is the object of the present invention to provide an improved device such as an Amsler grid for assisting a patient with macular degeneration to establish a baseline configuration associated with the amount of degeneration that has occurred in each eye and for monitoring subsequent changes in their vision.

It is a further object to provide an improved device such as an Amsler grid which is conveniently packaged to facilitate daily use by a patient.

It is another object of the present invention to provide an improved device such as an Amsler grid which maintains a patient's attention focused squarely on the grid so as to allow for a more accurate evaluation of the patient's vision.

It is another object of the present invention to provide an improved device such as an Amsler grid packaged in a convenient medium so as to be able to facilitate easy location of the grid in well traveled portions of the patient's residence.

In summary, the present invention is an improved ophthalmological self test unit for assisting in the self evaluation of the degenerative effects of certain eye disorders. The self diagnostic ophthalmological device includes a grid area having a re-writable surface which is fixably attached to a magnetic backed material for ease of attachment to any metallic surface such as might often be found on a refrigerator. Disposed on the grid surface is a central focusing means for assisting in the focusing of a patient's attention to the central portion of the grid structure. In an alternative embodiment a polar grid is utilized along with the central focusing means mounted upon the magnetic backed material.

BRIEF DESCRIPTION OF THE DRAWINGS

Initial objects and features of the invention will be more readily apparent from the following detailed description and appended claims when taken in conjunction with the drawings, in which:

DETAILED DESCRIPTION OF EXEMPLARY EMBODIMENTS

Figure 1:
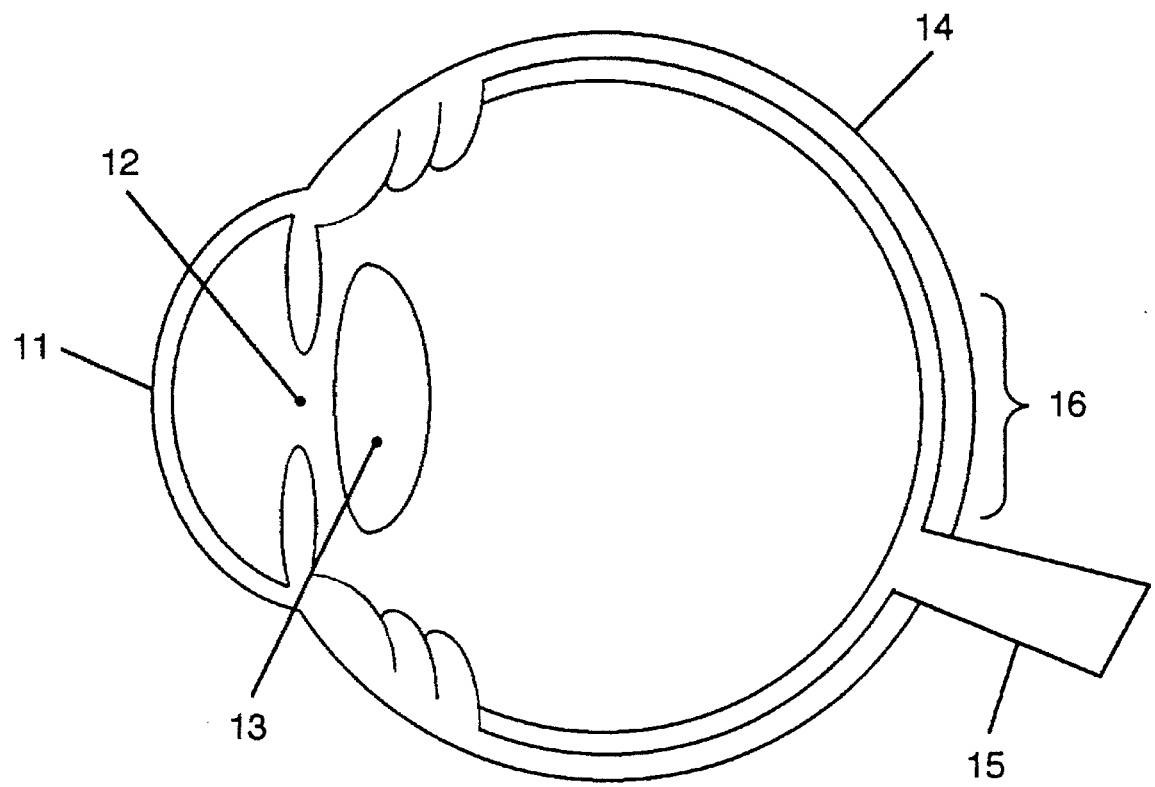
FIG. 1 is a cross section diagram a human eye.
Figure 2:
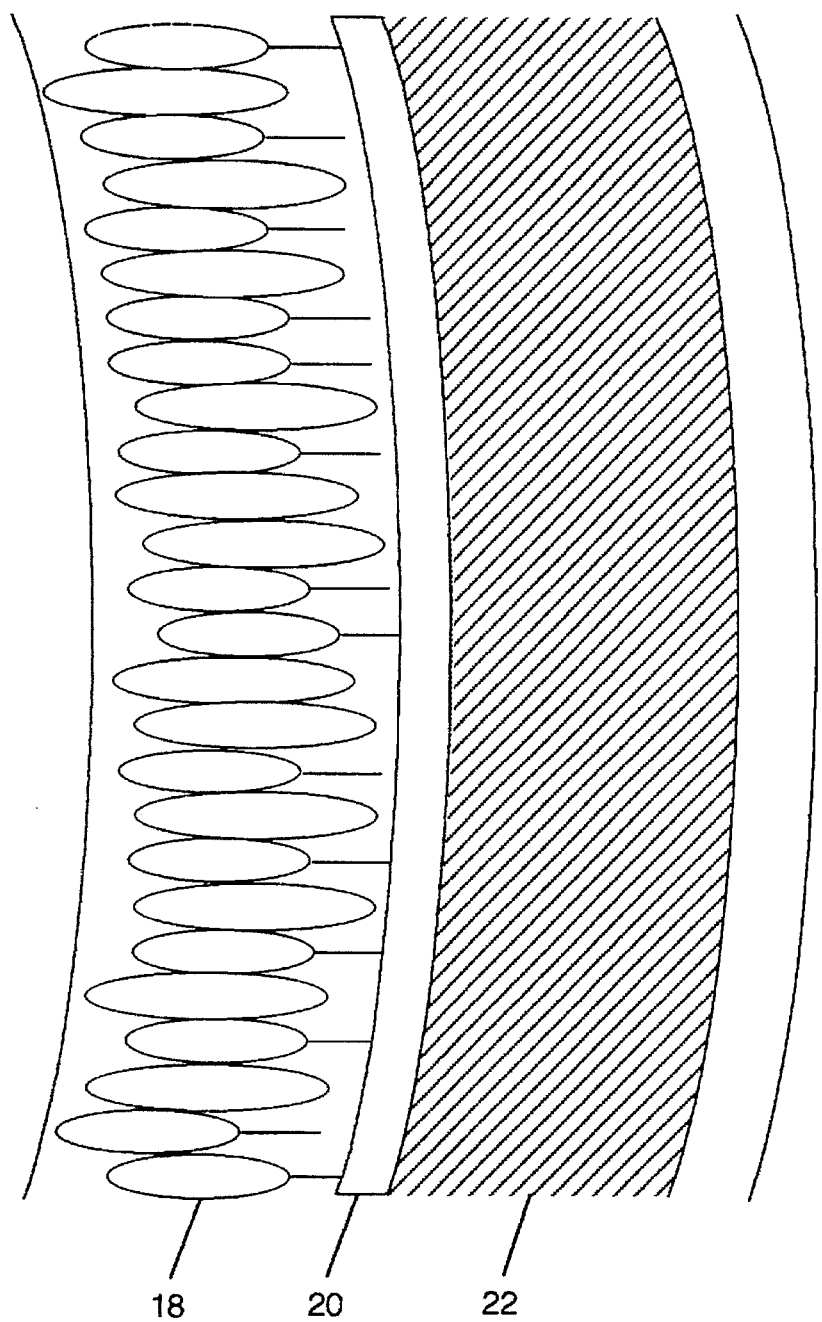
FIG. 2 is a cross section of a macular portion of the human eye.
Figure 3:
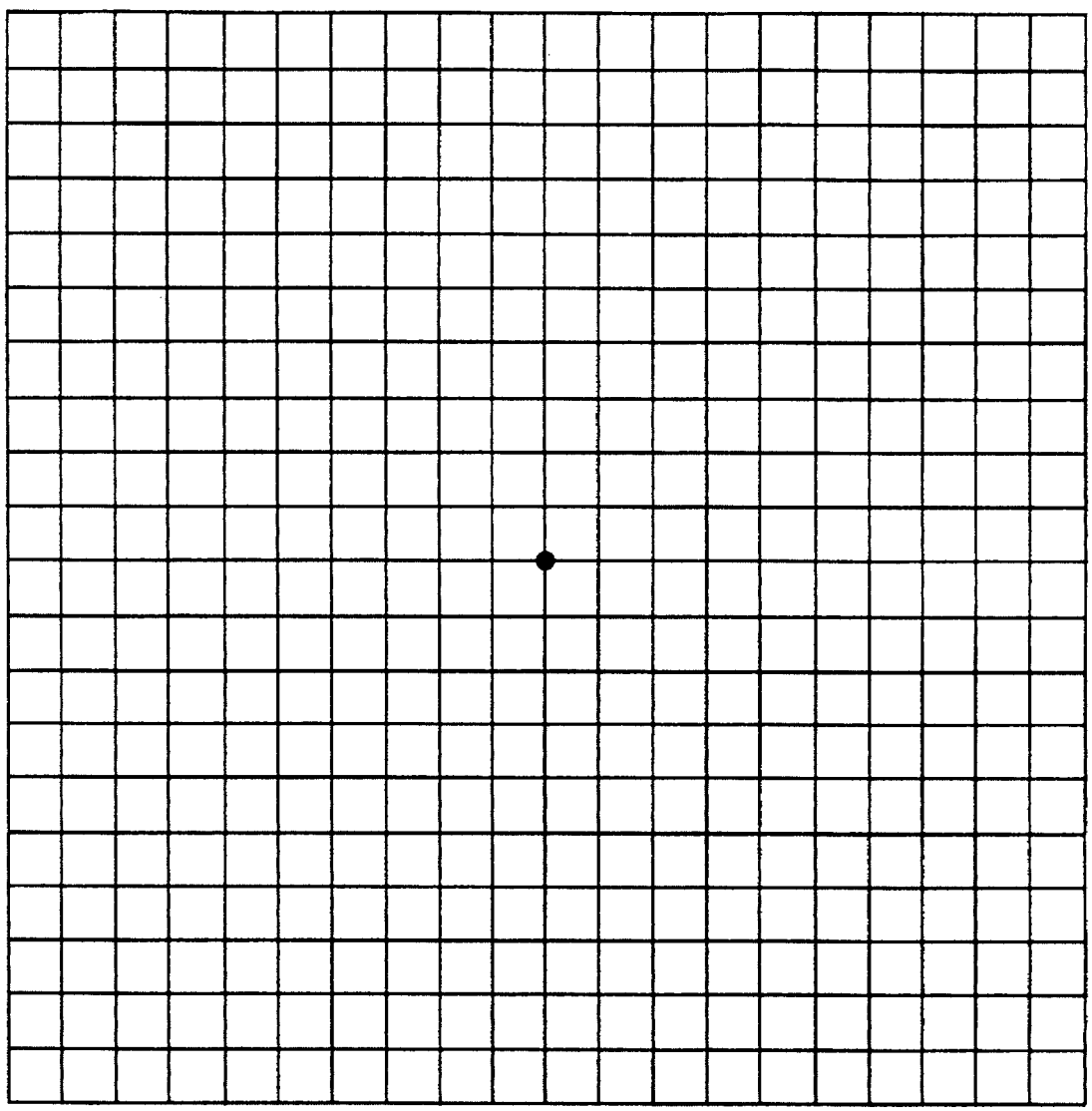
FIG. 3 is a prior art Amsler grid.
Figure 4:
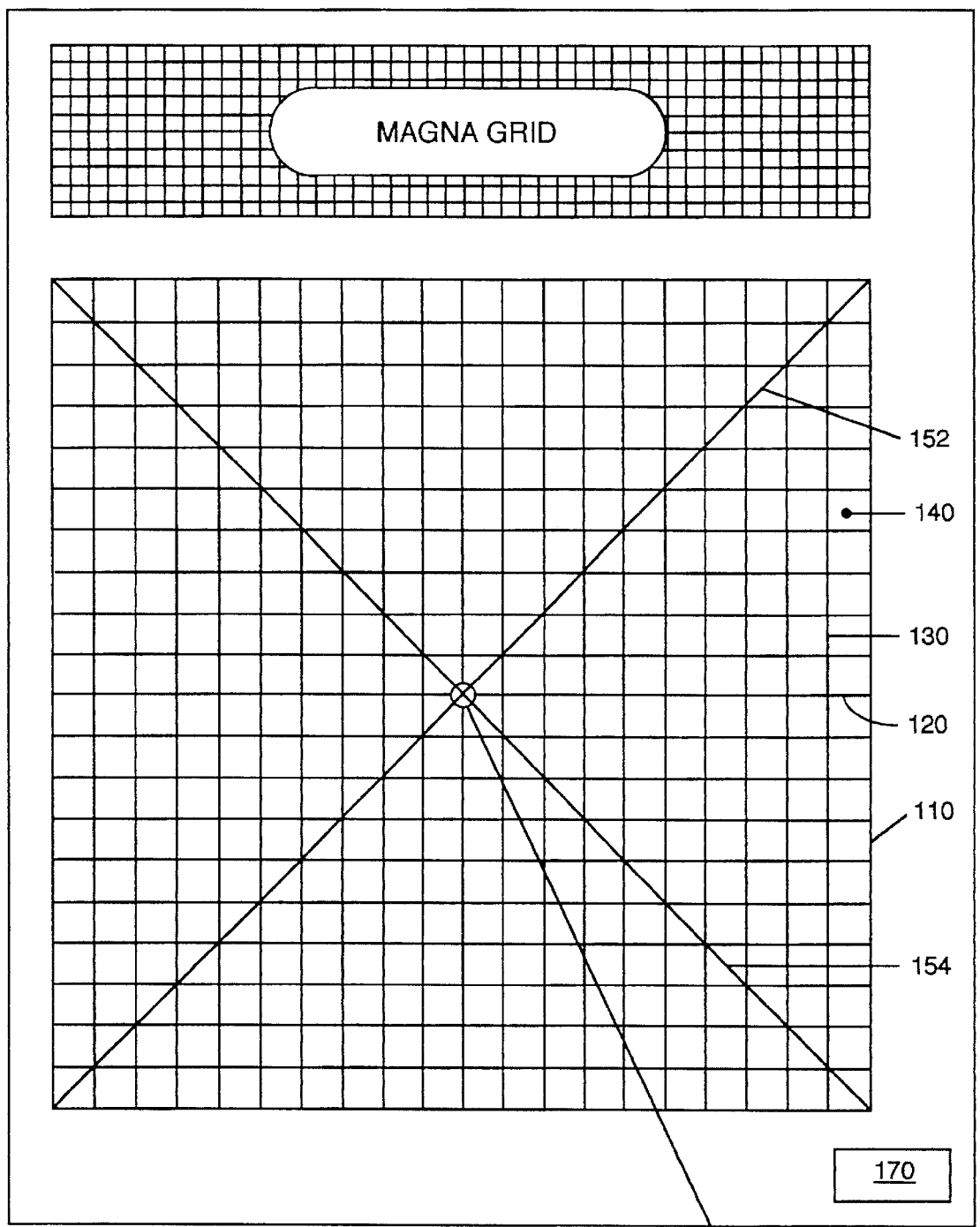
FIG. 4 is a grid structure according to one embodiment of the present invention.

Referring to FIG. 4, there is shown a diagram of a grid 100 according to one embodiment of the present invention. In this embodiment, the grid 100 is comprised of a grid area 110 which includes twenty horizontal lines 120 and twenty vertical lines 130. The horizontal and vertical lines are spaced to form one hundred individual boxes 140 in an overall grid size of 5"×5". Those ordinarily skilled in the art will recognize that as the grid size is made smaller, less area of the peripheral vision associated with a particular patient may be mapped by the diagnostic tool. Accordingly, a minimum grid size of approximately four inches square (4×4) should be utilized in order to effectively cover the region associated with the macula. Similarly, those ordinarily skilled in the art will recognize that grids exceeding or much bigger than represented will offer little or no help in diagnosing the progress of the disease because of the centrally located distortion effects associated with this particular eye disorder. Accordingly, a maximum grid size of approximately eight inches square (8×8) should be utilized. A grid size of five inches by five inches is preferred.

The spacing of the vertical/horizontal lines is done to accommodate the recognition by the patient of discrepancies from a norm. As the grid lines are drawn tighter and tighter together, the "busyness" of the grid tends to mask certain manifestations of the disorder. Accordingly, a grid square resolution on the order of between 0.05 and 0.09 square inches is recommended, with a grid size of 0.0625 square inches used in one embodiment.

Disposed on grid area 110 is focusing means 150. In one embodiment, focusing means 150 is comprised of a focusing pattern comprising a pair of red diagonal lines 152 and 154 which extend from the respective corners formed by grid horizontal and vertical lines 120 and 130 through the center of grid area 110. Alternatively, the focusing pattern may be a target cross hair as would be commonly found in a gun sight.

At the center of focusing means 150 is light source 156. In one embodiment, light source 156 is a light emitting diode (LED). In use, patients have reported that the centrally located light source coupled with red diagonal focusing lines serve to center the patient's attention fixedly on the central portion of the grid thereby allowing for repeatable test results. Alternatively, light source 156 may be a light bulb, a mirror, a rhinestone or other sufficiently light emitting or reflecting object as is known in the art. Light source 156 must be sized sufficiently small to avoid masking any centrally located vision distortion or defects. Accordingly, the light source should be sized to be less than 0.50 inches, and in one embodiment, the light source is an LED which is 3 mm (approximately 0.1 inches) in diameter.

Figure 5:
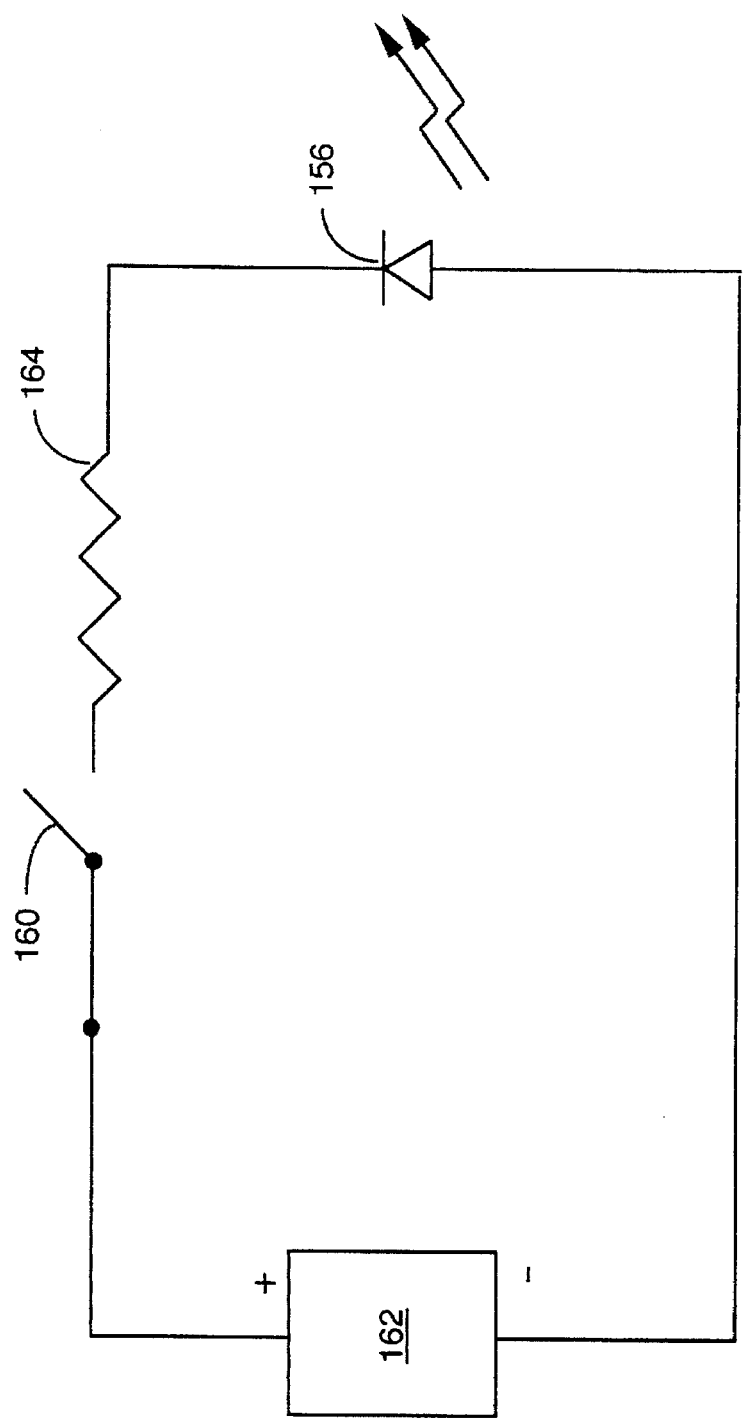
FIG. 5 is a block diagram of a circuit associated with the focusing means of one embodiment of the present invention.

Referring to FIG. 5, a circuit diagram associated with the electrical portion of focusing means 150 is shown. Light source 156 is attached at one end to a resistor 164 whose other end is coupled to the normally open contact of switch/relay 160. The common contact of the switch/relay 160 is in turn attached to the positive lead of power source 162.

Finally, the second lead from light source 156 is coupled to the negative lead of power source 162 forming a complete circuit. In the one embodiment, switch 160 is a single pole single throw manual switch, power source 162 is a lithium battery part number BR-2/3AA manufactured by Panasonic, resistor 164 is a 500 ohm resistor, and light source 156 is a light emitting diode part number BL-B5131-L manufactured by American Bright Optoelectronics Co. Those ordinarily skilled in the art will recognize that the parts were selected to minimize the overall profile of the components, while providing a sufficiently long life and duty cycle upon energization of light source 156 to allow a user to perform a complete test. As such, other similar parts may be substituted as is known in the art without departing from the true spirit of the present invention. Alternatively, switch relay 160 may be a Bipolar or Field Effect transistor, or an SCR, or any other electronic switch as is known in the art. Power Source 162 may alternatively be a solar cell, or other power source as is known in the art.

In operation, upon depressing manual switch/relay 160, power source 162 provides a voltage source at the positive lead to light source 156. Resistor 164 current limits the power source 162 providing for a sufficient amount of current to drive the LED, while minimizing the drain on the power source 162. Light source 156 will illuminate for as long as the manual switch is actuated, allowing for the user to easily focus on the center of the grid portion. Upon deactivating the manual switch/relay 160, the light source is powered, thereby conserving the battery power.

In an alternative embodiment, light source 156 is configured to flash over the period of activation. This is accomplished, for example, by providing a flasher control circuit 168 (not shown) between power source 162 and light source 156. In one embodiment, the flasher control circuit may be implemented by the use of capacitors to cause a simple saw tooth waveform to be delivered to the light source thereby resulting in the flashing action. Alternatively, a timer circuit employing, for example, a 555 timer is implemented between manual switch 164 and light source 156 to effectuate the flashing. Alternatively, a flashing LED may be utilized which incorporates the control circuit into the LED package. Flashing LEDs are available off the shelf from the American Bright Optoelectronics Co.

In one embodiment, power source 162, resistor 164, and relay 160 are packaged within a single block 170 as shown in FIG. 4. The block 170 is attached to the surface of grid 100 and allows for the easy removal and replacement of battery 162. In one embodiment, block 170 is comprised of molded plastic, but may be made of any other similar material as is known in the art. In addition, block 170 is fashioned to extend a minimal height above the surface of grid area 110 to minimize the occurrence of knocks or bumps to the device.

Figure 6:
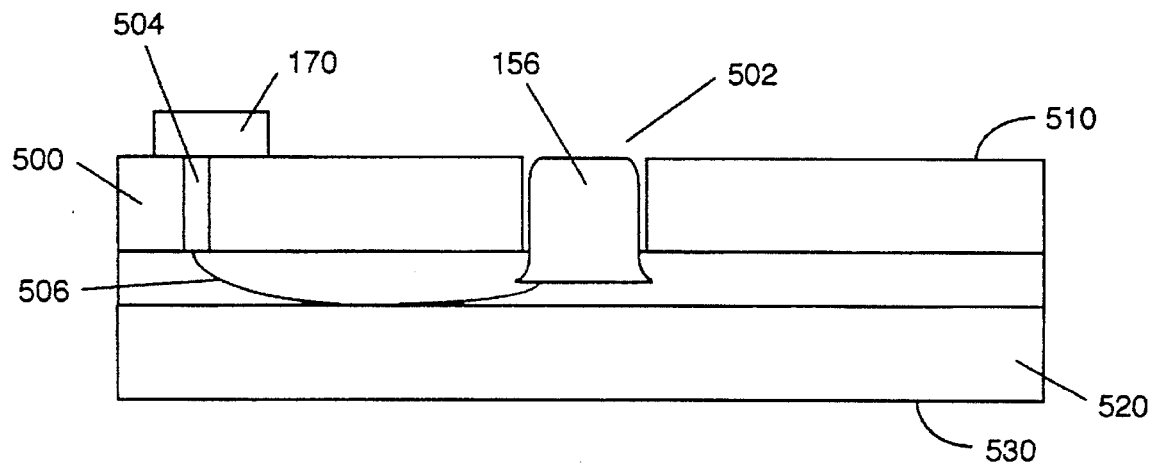
FIG. 6 is a cross section of the grid structure of FIG. 4.

Referring to FIG. 6, a cut away view of grid 100 is shown. In one embodiment, grid 100 is comprised of a top layer 500 having a first recess 502 for receiving light source 156 and aperture 504 for allowing interconnecting wires 506 to pass through top layer 500 for connection to power source 162 mounted in block 170. Top layer 500 includes an upper surface 510 which is made from a high contrast erasable, re-writable material which allows for the easy writing and recording of baseline information on the grid surface. The re-writable surface also allows for ease of erasing or correcting any mistakes made in the course of the diagnostic process. In use, this ease of correction feature has helped to encourage patients to map out affected portions of their vision which are abnormal, while non-erasable surfaces have been found to frustrate and even discourage patients from marking on the grid. As was disclosed above, ease of use coupled with patient comfort in recording baseline information have been found to be the keys to continued use of the test aid, and necessarily the early detection of degradations in the patient's vision. In one embodiment, upper surface 510 is comprised of vinyl. However, other materials which allow for ease of writing and erasing may be substituted as is known in the art.

Top layer 500 is disposed over a bottom layer 520 enclosing interconnecting wires 506 between the two layers. Bottom layer 520 includes a bottom surface 530 comprised of a magnetic material. The top layer is affixed to the bottom layer by any suitable glue material, such as an epoxy resin. In one embodiment, bottom layer 520 is a magnetic backed material composite part number 130 produced by Dowlng Miner Magnetics Corporation. The magnetic back material allows for the attachment of the grid to any metallic surface, such as on a refrigerator, which is located in a portion of the patient's house which is accessed daily. In addition, the magnetic back material allows the patient to quickly and easily store and locate the grid, while the re-writable/erasable surface allows for the preservation of the vital baseline information. In use, this type of easily accessible, conveniently storable and erasable configuration has been shown to encourage the patient to perform the self-diagnostic test on a daily basis.

Figure 7:
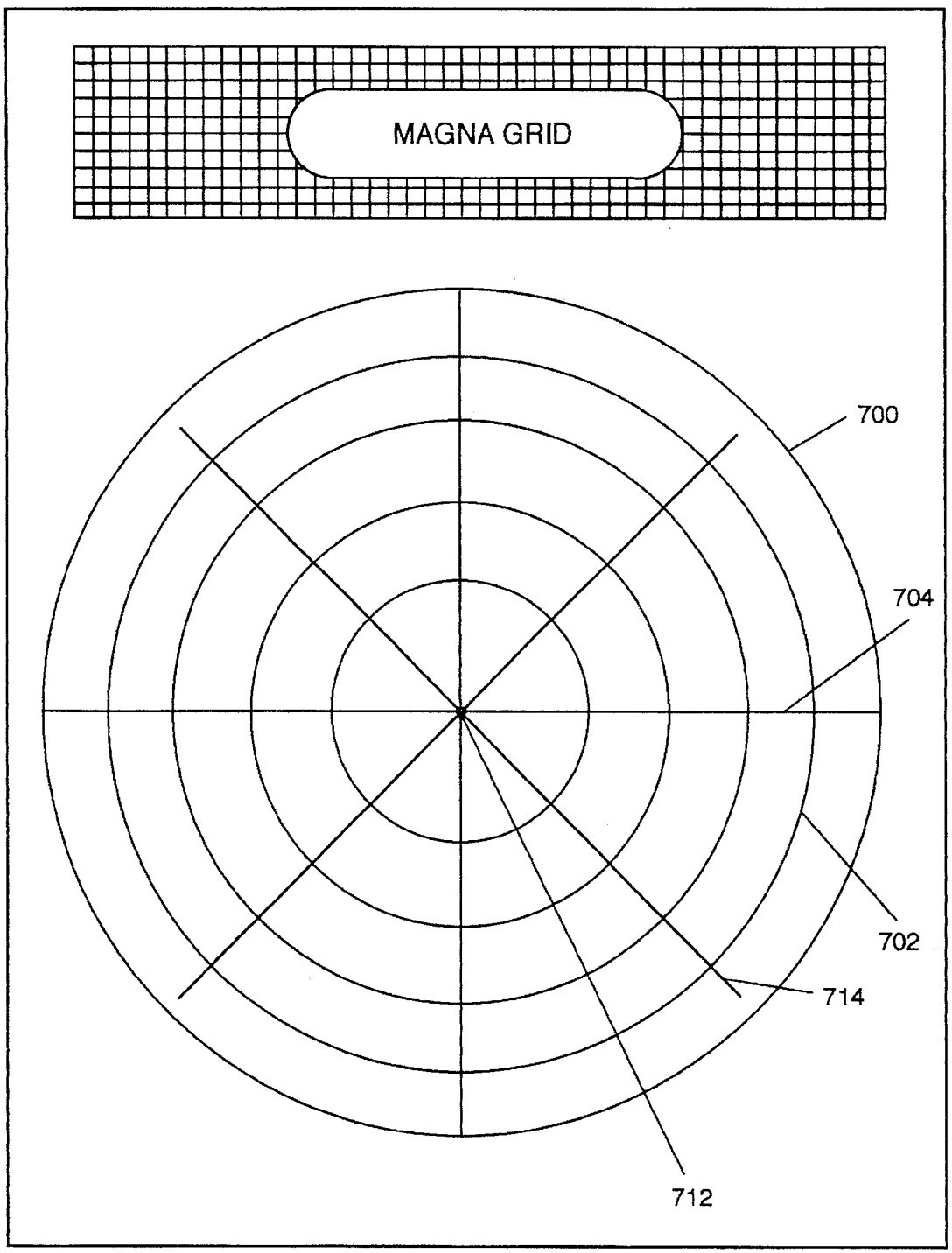
FIG. 7 is an alternative grid structure according to a second embodiment of the present invention.

Referring to FIG. 7, a second embodiment of the grid is shown. In this alternative embodiment, grid area 700 is comprised of a series of concentric circles 702 and radial lines 704. A focusing means 710 including light source 712 and diagonal centering lines 714 are include in this embodiment, and are similar to the focusing means disclosed above. In this embodiment, the attention centering function of focusing means 710 is augmented by the polar grid configuration due to the tunnel affect created by the concentric circles.

In operation, a patient will define a baseline characterization of his vision at his or her respective physicians's office in order to track the progress of this degenerative eye disorder. The baseline characterization is performed by marking on the re-writable/erasable surface of the grid the areas of distortion which have arisen in the particular person's vision as of a baseline time. Thereafter this baseline information may be readily compared to the present results so that the progress of the disease may be monitored.

In use, the grid is to be mounted to a metallic surface such as found on a common refrigerator door, in a well traveled location of the patient's home. The magnetic back mounting also minimizes the risk of misplacing the grid thereby losing the baseline information that has been developed and recorded on the grid device. The grid being adaptable for easy, convenient, and highly visible storage while not in use, will encourage the patient to repeat the test as necessary and to record all relevant information for discourse with a physician at the appropriate juncture. At the designated hour of a given day, the patient can quickly and easily locate the grid, and activate the light source to focus the patient's attention. The focusing means is activated by depressing the manual switch located on the casing. Thereafter, the patient may quickly and easily perform a test on each eye, comparing his or her current vision (and associated defects) against the baseline information stored on the grid. In the event any differences are detected over the baseline, the patient may document these new changes by marking on the grid the areas that have become affected and contact his or her respective physician.

The present invention has been described with reference to a few specific embodiments. The description is illustrative of the invention is not to be construed as limiting the invention. Various modifications may occur to those skilled in the art without departing from the true spirit and scope of the invention as defined by the pending claims.

What is claimed:

1. An ophthalmological self test apparatus for assisting in the daily evaluation of the human eye, the apparatus comprising:

a first layer, said first layer having a top and bottom surface and a centrally disposed aperture therebetween, said top surface having a grid pattern disposed thereon;

focusing means, said focusing means including a light source disposed in said aperture for allowing light to be emitted from said aperture at said top surface, and switching means coupled to said light source for activating said light source; and a magnetic second layer fixedly attached to said first layer for maintaining said self test apparatus upon attachment to a magnetically permeable surface.

2. The self test apparatus of claim 1 wherein said grid is comprised of a complementary number of horizontal and vertical lines.

3. The self test apparatus of claim 1 wherein said grid is polar including concentric circles and radial lines.

4. The self test apparatus of claim 1 wherein said switching means includes a first mechanical switch for activating said light source.

5. The self test apparatus of claim 4 wherein said switching means further includes a power source and a flashing control circuit, said power source coupled to said light source by said first mechanical switch, said flashing circuit coupled between said power source and said light source for causing said light source to flash upon activation of said mechanical switch.

6. The self test apparatus of claim 1 wherein said light source comprises a light emitting diode.

7. The self test apparatus of claim 1 wherein said top surface is a high contrast re-writable and erasable surface.

8. The self test apparatus of claim 1 wherein focusing means further includes a focusing pattern disposed on said top surface of said top layer and over said grid pattern, said focusing pattern including a plurality of lines extending from a periphery of said top surface toward said centrally disposed aperture.

9. The self test apparatus of claim 8 wherein said focusing pattern is a pair of diagonal lines.

10. The self test apparatus of claim 8 wherein said focusing pattern is a target cross hair pattern.

11. An ophthalmological self test apparatus for monitoring the progress of macular degeneration in the human eye, the apparatus comprising:

a first layer, said first layer having a top and bottom surface and a centrally disposed aperture therebetween, said top surface having a grid pattern disposed thereon;

focusing means, said focusing means including a light reflector disposed in said aperture for allowing light to be reflected from said aperture at said top surface toward said human eye when said apparatus is in use; and a magnetic second layer fixedly attached to said first layer for maintaining said self test apparatus upon attachment to a magnetically permeable surface.

12. The self test apparatus of claim 11 wherein said grid is comprised of a complementary number of horizontal and vertical lines.

13. The self test apparatus of claim 11 wherein said grid is polar including concentric circles and radial lines.

14. The self test apparatus of claim 11 wherein said light reflector comprises a rhinestone.

* * * * *